United States Patent [19]

Kolff et al.

[11] Patent Number: 4,663,049

[45] Date of Patent: May 5, 1987

[54] PROCESS FOR THERAPEUTIC DISSOCIATION OF IMMUNE COMPLEXES AND REMOVAL OF ANTIGENS

[75] Inventors: Willem J. Kolff; Udipi R. Shettigar, both of Salt Lake City, Utah

[73] Assignee: University of Utah, Salt Lake City, Utah

[21] Appl. No.: 627,961

[22] Filed: Jul. 5, 1984

[51] Int. Cl.$^4$ ............................................. B01D 13/00
[52] U.S. Cl. ..................................... 210/641; 210/651; 210/433.2
[58] Field of Search .................. 604/4, 5, 6; 210/645, 210/651, 641, 433.2

[56] References Cited

U.S. PATENT DOCUMENTS

| | | | |
|---|---|---|---|
| 3,788,319 | 1/1974 | Gillette | 128/214 B |
| 4,215,688 | 8/1980 | Terman et al. | 128/214 R |
| 4,223,672 | 9/1980 | Terman et al. | 128/214 R |
| 4,321,192 | 3/1982 | Jain | 260/122 |
| 4,322,275 | 3/1982 | Jain | 604/6 X |
| 4,350,156 | 9/1982 | Malchesky et al. | 604/6 |
| 4,375,414 | 3/1983 | Strahilevitz | 210/648 X |
| 4,401,430 | 8/1983 | Dorson, Jr. et al. | 604/4 |
| 4,411,786 | 10/1983 | Russell | 210/321.3 |

FOREIGN PATENT DOCUMENTS

82/03568  10/1982  PCT Int'l Appl. ................ 210/651

OTHER PUBLICATIONS

G. R. Currie et al., "Serum Mediated Inhibition of the Immunological Reactions of the Patient to His Own Tumour: A Possible Role for Circulating Antigen," Br. J. Cancer 26, 427–438 (1972).

Primary Examiner—Frank Spear
Attorney, Agent, or Firm—Workman, Nydegger & Jensen

[57] ABSTRACT

The present invention provides an improved method for treating blood to remove foreign substances such as immune complexes and free antigen. This is advantageously accomplished by separating a portion of a patient's blood as plasma, and acidifying the plasma to a pH below about 3.1 in order to cause the immune complexes to dissociate into antigen and antibody. After removing the antigen, the plasma is returned to the patient. Preferably, the patient's blood is substantially diluted prior to plasma separation, thereby substantially increasing the clearance rate of the plasma separator device and also washing off antigens bound to cellular blood components. Also, it is preferred that the plasma fraction is further diluted during the acidification step. Subsequent removal of excess fluid will cause substantial removal of free antigen. In a presently preferred process, the excess fluid volume is reduced by use of an ultrafiltration device capable of passing antigen, but not larger protein constituents of plasma. The resultant plasma solution is advantageously subjected to dialysis to simultaneously remove remaining antigen and to raise the pH back to a physiological level.

32 Claims, 1 Drawing Figure

PROCESS FOR THERAPEUTIC DISSOCIATION OF IMMUNE COMPLEXES AND REMOVAL OF ANTIGENS

BACKGROUND

1. The Field of the Invention

The present invention relates to methods for potentiating the immune system in patients having cancer or other diseases. More particularly, the present invention is directed to on-line purification of a patient's blood plasma in order to separate antigens from circulating immune complexes and to subsequently remove the free antigens so that the activity of the patient's lymphocytes may be unblocked.

2. The Prior Art

A normal human body has the ability to develop immunity against foreign substances, such as bacteria, viruses, toxins, and foreign tissues.

An immune response is initiated upon exposure and recognition of a substance as being foreign. (A foreign substance capable of eliciting an immune response is known as an "antigen"). Following this exposure and recognition, the body's lymphoid tissues begin developing specific globulin protein molecules, known as "antibodies," and the lymphoid tissues also produce specifically sensitized lymphocytes that are capable of destroying foreign cells.

It is well known that many types of malignant tumor cells are recognized as being "foreign" and initiate an immune response wherein the patient's body generates specific antibody and circulating cytotoxic lymphocytes. Yet, in cancer patients it is clear that the tumor is not destroyed. Because of this apparent inconsistency, a great deal of effort has been directed to studying the relationship between malignant tumor cells and the immune response.

One result of this research has been the discovery that tumor cells "shed" surface antigens into the patient's circulatory system where they react with specific antibodies, thereby forming an "immune complex." One result of shedding antigens into the patient's bloodstream is that these antigens tie up antibodies and lymphocytes that could otherwise attack the tumor cells. In advanced cancer patients, the level of free antigens in the patient's bloodstream can greatly exceed the capacity of the patient to generate antibody.

However, it has also been discovered that shedding of antigens results in a significant increase in the concentration of immune complexes in the cancer patient's bloodstream. It has been discovered that such an increase in the level of circulating immune complexes and free antigens in the patient's circulatory system suppresses or "blocks" the ability of specific cytotoxic lymphocytes to kill the tumor cells growing in the patient's body. The presence of elevated levels of immune complexes and free antigens are also thought to exert both qualitative and quantitative effects on the immune response by interacting with receptor sites on other types of cells involved in the immune response.

In an attempt to decrease the levels of circulating immune complexes and free antigens in the patient's circulatory system, and hence to "unblock" the patient's immune system, it has become increasingly common to subject seriously ill cancer patients to a series of plasma exchange treatments, commonly called plasmapheresis, wherein a substantial portion of the patient's plasma, containing unwanted circulating immune complexes, is separated from the cellular components of the patient's blood, and is discarded. A volume of previously stored plasma (or of a plasma substitute) approximately equal to the volume of discarded plasma is then infused back into the patient together with the patient's own cellular blood components in an effort to maintain proper blood viscosity, electrolyte balance, and the like. This process of plasma exchange has been successfully used to treat a variety of clinical conditions, such as toxemia, drug overdose, rheumatoid arthritis, and the like, as well as cancer.

However, while capable of removing circulating immune complexes from the patient's circulatory system, and thereby also overcoming the suppressive effects of these complexes on the patient's immune system, the use of plasma exchange treatments on a continuing basis is itself subject to significant disadvantages and dangers that have heretofore generally restricted this treatment for use only on critically ill patients where other alternatives do not exist.

For instance, one major disadvantage of the use of plasma exchange therapy has simply arisen from the lack of availability of replacement plasma. Further, the use of a donor's plasma substantially increases the likelihood of potential complications arising from infection, such as hepatitis, or Acquired Immune Deficiency Syndrome (generally know as "AIDS").

These donor-related problems can be avoided by use of a plasma substitute, i.e., a solution having a suitable electrolyte balance (and, preferably, also to which purified human albumin has been added). However, use of a plasma substitute generally results in a dramatic decrease in the concentration of immunoglobulins in the patient's bloodstream, since a substantial level of immunoglobulins are discarded with the plasma separated during the plasma separation step.

One effect of this reduction is a rebound phenomenon wherein the patient's body vastly increases its production of antibodies. However, a large excess of antibodies tends to mask all the surface antigens of the tumor cells, thereby interfering with the action of cytotoxic lymphocytes. Although some attempts have been made to prevent this rebound phenomenon by administering large replacement doses of immunoglobulins, this approach has not been entirely satisfactory for the same reasons that use of donor plasma is not completely satisfactory.

Additionally, despite great care, a patient subjected to repeated plasma exchange therapy is extremely likely to suffer significant variations in blood viscosity and in fluid and electrolyte balance, depression of immunoglobulins (particularly IgG), clotting disorders, immunological side effects, and/or anemia. In a patient already seriously ill from an advanced tumor, such irregularities are very dangerous. It is believed that such variations may also contribute to metastasis of a previously localized tumor.

Yet another disadvantage of conventional plasma exchange is the inability of that technique to remove antigens that are bound to cells. In cancer patients, it is common for antigens to become bound to the surfaces of lymphooytes, thereby inactivating the lymphocytes. In order to restore the cytotoxioity of these lymphooytes, it has in the past been necessary to conduct a procedure such as removal of the lymphocytes by lymphocytaphoresis followed by either replacement with donor-lymphocytes or "washing off" the antigens from the lymphocytes followed by return of the washed-off lymphocytes to the patient. However, these latter techniques are cumbersome, particularly when it is realized that they must be performed in addition to plasma exchange as set forth above.

In view of the foregoing, it will be appreciated that it would be a significant advance in the art of cancer treatment if improved procedures could be provided for removing immune complexes and free antigens from a patient's circulatory system without causing the serious side effects presently encountered as a result of plasma exchange therapy.

PRINCIPAL OBJECTS AND BRIEF SUMMARY OF THE INVENTION

In view of the foregoing problems experienced with conventional plasma exchange treatments, it is a primary object of the present invention to provide methods for removing circulating bound antigens (antigens bound to antibodies to form antigen-antibody complexes) from a patient's circulatory system without requiring a donor's plasma or purified plasma fractions as substitution fluid.

It is another primary object of the present invention to provide methods for potentiating the patient's immune system by removing circulating antigens from the patient's plasma but returning the patient's albumin and other useful plasma constituents to the patient's circulatory system.

Yet another principal object of the present invention is to provide methods for improving the clearance rate of a plasma separator by diluting the blood with a dilution fluid (an electrolyte solution of physiological concentration) before passing the blood to the plasma separator.

Yet another principle of the present invention is to provide methods for washing antigens off of lymphocytes or other cells to which they are bound by diluting the patient's blood with a dilution fluid before passing the blood to the plasma separator, and then returning the washed cells to the patient.

These and other objects and features of the present invention will become more fully apparent from the following description and appended claims taken in conjunction with the accompanying drawings.

In accordance with the foregoing principal objects, the present invention is directed to an improved process for removing immune complexes and antigens (or bound antigens and free antigens) from a patient's blood, involving the steps of separating plasma containing immune complexes and antigens from the cellular blood components; subjecting the plasma to treatment with a mild acid in order to effect dissociation of the immune complexes into antigen and antibody; removing the antigens from the plasma; and returning the treated plasma to the patient's bloodstream together with the cellular blood components.

In addition to the foregoing, it has been found that the efficiency of the plasma separation step can be significantly improved by substantially diluting the patient's blood prior to effecting plasma separation. This excess fluid is then removed in a subsequent treatment step before the treated plasma is recombined with the cellular blood components thereby maintaining proper blood viscosity and composition.

It has been found that such a dilution step also acts to cause the release of antigens bound to cells, such as lymphocytes. Often, the binding of antigens to cells inactivates the cells. The release of antigens or "washing" of the cells restores the activity of the cells. Hence, the dilution of blood prior to separating the cellular blood components from blood plasma causes the release of antigens bound thereto, and assists the patient by restoring the activity of previously inactivated cells.

DETAILED DESCRIPTION OF THE INVENTION

Figure 1:
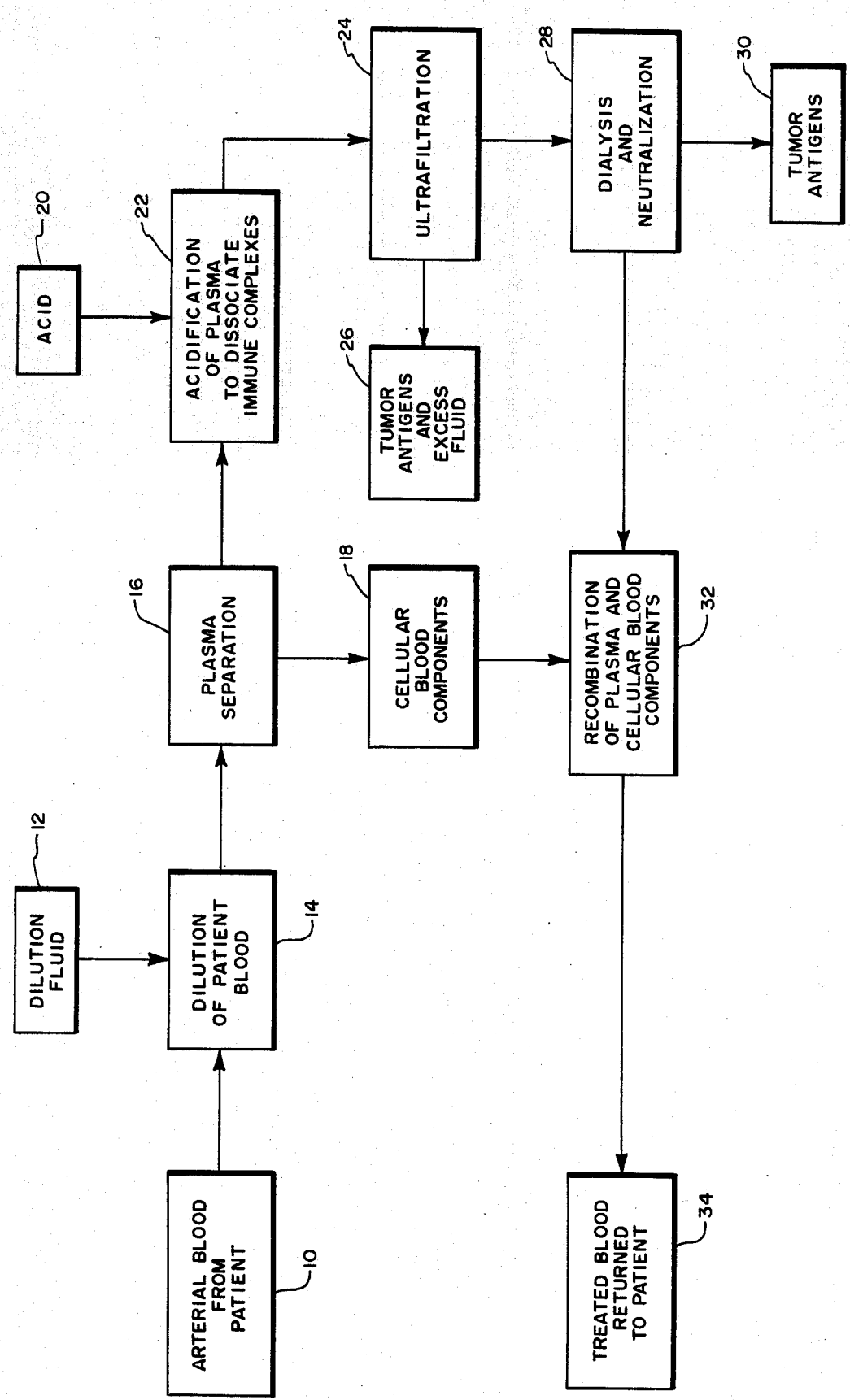
FIG. 1 is a flow chart of a presetnly preferred process of the present invention, setting forth various presently preferred steps involved in removing antigens from a patient's blood.

Reference is next made to the drawing, which illustrates the flow path of a presently preferred process of the present invention. In the following discussion, for the sake of brevity the process of the present invention will be described primarily in the context of removal of tumor antigens from cancer patients. However, it is to be understood that the present invention is also applicable to removal of other types of antigens from patients suffering from other types of diseases As mentioned above, it has been long known that the concentration of circulating tumor antigen and immune complexes are substantially higher in the blood of cancer patients than in a normal healthy person. It is also well-known that such elevated levels of circulating tumor antigen and immune complexes act to suppress or "block" the ability of a patient's immune system, and particularly cytotoxic lymphocytes, to combat the tumor. Reducing the levels of tumor antigen and immune complexes "unblocks" the ability of the patient's immune system to combat the tumor.

In contrast to conventional processes which reduce the level of circulating immune complexes simply by means of plasma exchange, wherein separated plasma containing immune complexes is simply discarded and replaced by either donor plasma or a plasma substitute, the present invention is directed to a process of plasma treatment wherein the patient's plasma is treated so as to dissociate the offending immune complexes into the respective antibody and antigen. Tumor antigen (both dissociated from the immune complex and free antigen in the plasma) is then separated from the plasma and the treated plasma is returned to the patient. Advantageously, the specific antibody is also returned to the patient where it can be reused.

As will be better appreciated from the discussion which follows hereinbelow, dilution of the patient's blood with a dilution fluid prior to separation of the plasma for treatment is also extremely advantageous because such dilution serves to wash off antigens bound to the surface of cellular blood components. This increases the clearance of antigens from the patient's bloodstream and also restores the activity of the cellular blood components. Thus, use of a dilution step allows return of purified cellular components to the patient as well as return of purified plasma.

As with conventional plasma exchange procedures the process of the present invention begins with collection of arterial blood, indicated in FIG. 1 by reference numeral 10.

In the past, such arterial blood has generally been pumped by means of a peristaltic pump (or occasionally by techniques using the patient's own arterial blood pressure), directly into a plasma separator device capable of separating a portion of the blood plasma from the cellular components of the blood. Under these conditions, a typical plasma separator is capable of separating about 10 percent to 30 percent of the blood volume as plasma.

Although this conventional method of achieving plasma separation is relatively effective, because of the low rate of plasma separation, it is necessary to recirculate the portion of the blood returned to the patient through the plasma separator device several times in order to reduce the level of circulating immune complexes to a suitable level. An important feature of the present invention is the ability to significantly increase the clearance rate of immune complexes from a patient's blood, thereby resulting in more efficient and shorter plasma treatment sessions.

Such an increase in the clearance rate of the plasma separator device is advantageously accomplished by mixing the patient's arterial blood 10 with a dilution fluid 12 in order to form substantially diluted blood 14 prior to passing it through a plasma separator device 16. It has been found that diluting the blood in this manner prior to separating a plasma fraction increases the clearance rate by about 200 percent to 400 percent, thereby enabling a plasma separator device to separate about 40 percent to 60 percent of the diluted blood volume as a plasma fraction.

Additionally, it has been discovered that dilution of the patient's blood prior to passing it through the plasma separator has the beneficial effect of washing antigens from cellular blood components to which they are bound. This important feature of the present invention has the dual effect of increasing the clearance of antigen from the patient's bloodstream and also of restoring activity to the patient's cellular blood components.

Since a portion of the dilution fluid will be returned to the patient together with the cellular blood components, a suitable dilution fluid should be similar in composition to normal blood plasma. It should also have a pH of about 7.3 so that it will not alter the normal physiological pH of blood. However as will be better appreciated from the following discussion, the process of the present invention substantially conserves protein present in the original undiluted blood, making it necessary to provide only smaller molecular weight constituents of plasma as components of the dilution fluid. A suitable composition for a dilution fluid is set forth in Table I.

TABLE I

| Composition of Aqueous Dilution Fluid | |
|---|---|
| Component | Concentration |
| Sodium | 140.0 milliequivalents per liter |
| Potassium | 4.0 milliequivalents per liter |
| Chloride | 110.2 milliequivalents per liter |
| Acetate/bicarbonate | 35.0 milliequivalents per liter |
| Magnesium | 1.2 milliequivalents per liter |
| Glucose | 8.0 millimoles per liter |

Once the plasma has been separated from the cellular blood components 18, another important feature of the present invention is reduction of the level of immune complexes and free antigens in the separated plasma and then return of the treated plasma to the patient's circulatory system, thereby avoiding the need to infuse the patient with donor plasma or a plasma substitute. This procedure avoids the dangers of introducing donor-induced infections or reactions, and also minimizes the loss of important plasma protein constituents.

Further, in contrast to conventional plasma exchange therapy, which simply removes the immune complex from the patient's bloodstream by disposing of patient plasma, the present invention actually potentiates the ability of the patient to combat the tumor.

This potentiation is accomplished by effecting dissociation of the immune complex into tumor antigen and specific antibody, followed by removal of the dissociated antigen from the plasma and return of the antibody to the patient's bloodstream. Thus, in the case of a malignant tumor not only is the patient's immune system "unblocked" by reducing the serum level of circulating immune complexes, thereby permitting cytotoxic lymphocytes to assist in combatting the tumor cells, but specific antibody capable of attacking the tumor is returned to the patient's bloodstream where it can continue to participate as a component of the patient's immune response.

Although any of several methods for dissociating the immune complex could be utilized, the presently preferred method is to add an appropriate amount of an acid solution 20 to the separated plasma in order to reduce the pH of the resultant plasma solution to about 3.1; at this pH the immune complexes readily dissociate into free antibody and antigen, as indicated by reference numeral 22, yet no damage is done to the plasma protein components.

Having effected dissociation of the immune complexes, the tumor antigens (both dissociated and free antigens originally present in the plasma) may then be removed from the plasma, and the plasma returned to the patient, although it will be appreciated that before the plasma may be returned to the patient, it must be returned to the normal physiologial pH of 7.3 and the excess volume of fluid added during the dilution step and acidification step must be removed.

Again, it will be appreciated that a number of methods may be utilized to effect these procedures. Nevertheless, it is presently prefered that these tasks be accomplished in two steps as set forth below.

First, as indicated in FIG. 1 by reference numeral 24, it is preferred that the acidified plasma be passed through an ultrafiltration device capable of passing antigens into the filtrate along with excess solution, but not capable of passing antibody or other important protein components. Advantageously, this may be accomplished by use of a membrane filter capable of passing molecules having a molecular weight less than about 50,000 to 70,000 daltons.

In order to effect the separation, the acidified plasma is introduced into the ultrafiltration device under pressure and under a controlled flow rate. Adjusting the flow rate and pressure will permit adjustment of the volume of fluid that passes through the filter for discard, thereby providing a simple method for removing the excess volume 26 of plasma caused by addition of dilution fluid 12 and acid 20. Since the tumor antigen will be relatively evenly distributed throughout the diluted plasma fraction that is introduced into the ultrafiltration device, the percentage of tumor antigen removed in this step will approximate the percentage of excess fluid removed.

The portion of the plasma continuing through the ultrafiltration device containing antibody and other plasma protein constituents will, of course, still contain significant amounts of tumor antigen. Accordingly, the plasma is next advantageously subjected to dialysis 28 in order to raise the pH of the plasma from a pH of 3.1 to 7.3, and also to substantially remove the remaining antigens 30. Preferably, a bicarbonate buffered solution is used as the dialysate solution so that the pH of the plasma can be raised to a physiological pH of 7.3 concurrently with removal of tumor antigen. Advantageously, the dialysate should be heated to about 38° C. (or even higher) so that when the treated plasma is remixed with the cellular blood components 18, the resultant treated blood 32 will be at a temperature suitable for return to the patient 34.

The capacity of the present invention to remove immune complexes and tumor antigens from a patient's bloodstream can best be understood by reference to a representative example:

EXAMPLE I

An arterial line is established to a patient capable of drawing about 80 milliliters of blood per minute. A dilution fluid having the composition set forth in Table I is mixed with the patient's blood at the rate of about 50 milliliters per minute, resulting in about a 40 percent dilution. Under these conditions the flow rate of diluted blood to the plasma separator device is about 130 milliliters per minute.

A plasma separator device is much more efficient with diluted blood than with normal blood taken directly from a patient. As mentioned above a plasma separator device is capable of separating no more than about 30 percent of undiluted blood as plasma, meaning that a conventional plasmapheresis circuit is capable of separating only about 24 milliliters of plasma per minute.

In contrast, when diluting patient blood by about 40 percent as indicated above the separator device is capable of separating better than 50 percent of the blood volume as plasma. In the present situation, this means that about 70 millimeters of plasma will be separated per minute from the 130 milliliters per minute of diluted blood passing through the plasma separator device, with about 60 milliliters per minute of cellular components and plasma being passed through the separator for ultimate return to the patient.

Once a plasma fraction has been obtained it is treated with acid in order to dissociate the immune complex preparatory to removing antigen. Although various weak acids may be used, e.g., hydrochloric acid or a citrate solution, it is presently preferred to use a 0.74 percent hydrochloric acid solution. As will be better appreciated from the subsequent discussion, the acid solution should also contain the substances set forth in Table I to avoid diluting the concentration of these substances in the plasma ultimately returned to the patient. It has been determined that addition of about 50 milliliters per minute of 0.74 percent hydrochloric acid to a plasma fraction having a pH of 7.3 and flowing at the rate of about 70 milliliters per minute is capable of reducing the pH of the resulting plasma solution to about 3.1. The resulting flow rate is 120 milliliters per minute.

The use of a weak as opposed to a strong acid solution is advantageous for at least two reasons. First, use of relatively large amounts of a weak acid rather than small amounts of a strong acid avoids the possibility of localized areas of very high acidity that could cause damage to plasma proteins before the acid is fully mixed with the plasma.

Additionally, use of a weak acid contributes to significantly diluting the plasma. When the excess solution is subsequently removed by ultrafiltration, removal of large amounts of excess fluid contributes to removal of large amounts of antigen.

For instance, in the present example the flow of plasma from the plasma separator device is about 70 milliliters per minute, and the flow of the cellular blood fraction is about 60 milliliters per minute. Since blood is withdrawn from the patient at a rate of 80 milliliters per minute, the volume of the plasma fraction must be reduced to about 20 milliliters per minute before recombination with the cellular blood fraction, so that the volume of blood returned to the patient equals the volume removed. Reduction of 50 milliliters per minute of plasma through an ultrafiltration device (the amount of reduction needed to go from a flow rate of 70 milliliters per minute) to 20 milliliters per minute involves about a 70 percent reduction in plasma volume. Since the distribution of antigen in the plasma solution is relatively constant, clearly this procedure would also result in a 70 percent reduction in the total number of antigens originally present in the acidified plasma.

However, by diluting the plasma fraction to a flow rate of 120 milliliters per minute during the acidification step, the plasma volume will be reduced by about 83 percent in order to reduce plasma flow to the desired flow rate of 20 milliliters per minute, thereby improving the efficiency of antigen removal during ultrafiltration by about 13 percent. This results, coincidentally, in about an 83 percent reduction in the total number of antigens originally present in the acidified plasma.

After ultrafiltration, the flow rate of plasma will be at the desired level of about 20 milliliters per minute. By this stage, only about 17 percent of the tumor antigen remains in the plasma. This small amount is easily removed by passing the plasma through a dialyzer unit. Advantageously, use of a bicarbonate solution as a dialysate solution will result in diffusion of bicarbonate into the plasma, thereby raising the plasma pH concurrently with diffusion of tumor antigen from the plasma and into the dialysate solution. Finally, the treated plasma is remixed with the cellular blood fraction, and the treated blood, now clear of immune complexes and substantially clear of free antigen, but containing specific antibody and other important plasma proteins, is returned tc the patient.

Utilizing the procedure set forth in Example I, it is anticipated that a typical treatment session will last about 3 hours. During that time, about 14.4 liters of blood will be circulated through the extracorporeal circuit. Since the average adult has a total blood volume of about to 5 to 6 liters of blood, this results in a turnover of about 2 to 3 times the patient's total volume of blood. In some instances, with advanced cancer patients it is anticipated that three treatments per week will be required initially, although this will likely be reduced after a few weeks to only one treatment per week. With other patients it may be desirable to conduct the process continuously for several weeks, an option not reasonably available when practicing conventional plasma exchange therapy. It is expected that in some instances the foregoing treatment regimen will allow the parient's immune system to destory the tumor, and in others, it will assist chemotherapy or radiation therapy.

It will be appreciated from the foregoing that a physician will have a tremendous amount of flexibility in designing an actual treatment procedure. The flow rate of dilution fluid may be adjusted to give a suitable blood viscosity and flow rate through the plasma separator unit, and the flow rate of acid solution added during the acidification step may similarly be adjusted to regulate the amount of antigen removed during ultrafiltration.

Although it has been indicated that it is presently preferred to use a two-step process of antigen and excess fluid volume reduction by ultrafiltration followed by dialysis, it will be appreciated that alternative means may be utilized for removing antigen and excess fluid in keeping with the present invention. For instance, it would be possible to pass acidified plasma directly into a high flux dialyzer capable of simultaneously removing excess fluid and antigen. However, because of the much higher levels of antigen initially present in the plasma introduced into such a dialysis unit, concurrent neutralization of the plasma would likely result in recombination of significant amounts of antigen and antibody, thereby increasing the resultant level of immune complexes in the blood returned to the patient following treatment.

From the foregoing, it will be appreciated that the present invention avoids the disadvantage of conventional plasma exchange therapy of requiring replacement plasma by way of a donor or a plasma substitute. This avoids risks that the patient will contract hepatitis, AIDS, or other donor-related infections, yet also insures that important protein constituents of plasma, and particularly immunoglobulins, will not become depleted in the patient's system even after a number of plasma treatment sessions or after an extended period of continuous treatment.

The present invention assists the cancer patient in two very important ways. First, the level of circulating immune complexes is dramatically reduced, thereby "unblocking" the ability of the patient's immune system to combat the cancer. In this respect, the present invention has the same effect as conventional plasma exchange.

However, unlike conventional plasma exchange therapy, the present invention removes only the offending portion of the immune complex -- it removes only the antigen. Further, it is far more effective at removing free antigen from the patient's bloodstream than is straight plasma exchange, because a much larger volume of plasma is treated in connection with the present invention than is removed in a plasma exchange process. Further, in addition to removing antigen from the patient's plasma, the present invention is capable of removing substantial amounts of antigens bound to cellular blood components, thereby restoring cytotoxicity of such cells. Finally, specific antibody (as well as other immunoglobulins originally present in the patient's blood) is returned to the patient where it can combine with and remove additional antigens from the patient's body.

It is to be understood that the present invention also has the capability of treating patients suffering from diseases other than cancer, or to remove toxins in a patient's blood or bound to plasma protein due to such occurrences as liver failure, digitoxin intoxication and various drug overdoses (e.g., overdoses of drugs such as cyelobarbital, butobarbital, phenobarbital, and phenytoin), or poisoning cases (such as poisoning by paraquat).

In view of the foregoing, it is to be understood that the present invention may be practiced in various ways without departing from its spirit or essential characteristics. The foregoing description is to be considered in all respects only as illustrative and not restrictive, and the scope of the invention is indicated by the appended claims. All modifications or changes which come within the meaning and range of equivalency of the claims are to be embraced within their scope.

What is claimed and desired to be secured by United States Letters Patent is:

1. A method for removing antigens from a patient's circulatory system, comprising the steps of:
   obtaining blood containing antigens from a patient;
   diluting the blood by adding a physiologically compatible electrolyte solution containing low molecular weight constituents of plasma so as to wash off at least a portion of the antigens from cellular components present in the blood prior to plasma separation;
   separating a plasma fraction from the cellular components of the diluted blood, said separated plasma containing antigens;
   removing the antigens from the plasma;
   removing excess plasma fluid without removing substantial amounts of plasma protein so as to reduce the volume of plasma;
   mixing the reduceed volume of plasma with the cellular blood components; and returning the treated blood to the patient.

2. A method for removing antigens from a patient's circulatory system as defined in claim 1, where from about 40 percent to about 60 percent of the diluted blood is separated as a plasma fraction.

3. A method for removing antigens from a patient's circulatory system as defined in claim 1 comprising the further step of adding a substantial amount of a dilution fluid to the separated plasma prior to removing the antigens so as to substantially dilute the concentration of antigens per unit of plasma, and wherein the step of removing excess plasma fluid is conducted in a manner such that a portion of the antigens are removed with said excess plasma fluid.

4. A method for removing antigens from a patient's circulatory system as defined in claim 1, wherein the excess plasma fluid is removed by passing the plasma fraction through ultrafiltration means capable of passing the antigens together with plasma fluid into the filtrate, but not capable of passing plasma proteins.

5. A method for removing antigens from a patient's circulatory system as defined in claim 4, wherein the plasma passing through the ultrafiltration means is passed through dialysis means to remove additional antigens.

6. A method for removing antigens from a patient's circulatory system as defined in claim 3, wherein the excess plasma fluid is removed by passing the plasma fraction through ultrafiltration means capable of passing the antigens together with plasma fluid into the filtrate, but not capable of passing plasma proteins.

7. A method for removing antigens from a patient's circulatory system as defined in claim 6, wherein the plasma passing through the ultrafiltration means is passed through dialysis means to remove additional antigens.

8. A method for removing antigens from a patient's circulatory system as defined in claim 1, wherein the antigens are tumor antigens.

9. A method for removing antigens from a patient's circulatory system as defined in claim 1, wherein the antigens are a drug.

10. A method for removing antigens from a patient's circulatory system as defined in claim 1, wherein the antigens are toxins.

11. A method for removing circulating antigens from a patient's circulatory system, comprising the steps of:
obtaining from a patient blood containing immune complexes;
separating a portion of the plasma component of the blood from the cellular components of the blood, said separated plasma containing immune complexes;
mixing a sufficient volume of an acid to the separated plasma in order to reduce the pH of the plasma to a pH such that the immune complexes in the plasma will dissociate into respective antigens and antibodies;
removing the antigens from the plasma;
mixing the treated plasma with the cellular blood components; and
returning the treated blood and antibodies contained therein to the patient.

12. A method for removing circulating antigens from a patient's circulatory system as defined in claim 11, wherein the step of adding acid to the separated plasma comprises lowering the pH of the plasma to a pH of about 3.1.

13. A method for removing circulating antigens from a patient's circulatory system as defined in claim 12, wherein the acid used is dilute hydrochloric acid.

14. A method for removing circulating antigens from a patient's circulatory system as defined in claim 11, wherein a substantial amount of acid solution is added to the separated plasma so as to substantially dilute the concentration of antigens per unit of plasma, and further comprising the step of removing excess plasma fluid in a manner such that a portion of the antigens are removed with said excess plasma fluid.

15. A method for removing circulating antigens from a patient's circulatory system as defined in claim 14, wherein a sufficient amount of acid solution is added such that the concentration of antigens per unit of plasma is diluted to within the range of about 30 percent to about 70 percent of the concentration of antigens in the plasma prior to dilution.

16. A method for removing circulating antigens from a patient's circulatory system as defined in claim 11, comprising the further step of adding a substantial amount of a dilution fluid to the patient's blood prior to separating a portion of the blood as plasma so that an increased percentage of the blood volume is separated as plasma during the plasma separation step.

17. A method for removing circulating antigens from a patient's circulatory system as defined in claim 11, comprising the further step of adding a substantial amount of a dilution fluid to the patient's blood prior to separating a portion of the blood as plasma so that a significant number of antigens bound to cellular blood components will become detached from such cellular blood components.

18. A method for removing circulating antigens from a patient's circulatory system as defined in claim 16, wherein a sufficient amount of dilution fluid is added to the blood so as to dilute the concentration of immune complexes per unit of blood to within the range of about 30 percent to about 70 percent of the concentration of immune complexes the blood prior to dilution.

19. A method for removing circulating antigens from a patient's circulatory system as defined in claim 18, wherein about 40 percent to about 70 percent of the total volume of diluted blood is separated as plasma.

20. A method for removing circulating antigens from a patient's circulatory system as defined in claim 16, wherein the dilution fluid is a physiologically compatible electrolyte solution containing low molecular weight constituents of normal plasma.

21. A method for removing circulating antigens from a patient's circulatory system, comprising the steps of:
obtaining from a patient blood containing immune complexes;
separating a portion of the plasma component of the blood from the cellular components of the blood, said separated plasma containing immune complexes;
mixing a sufficient volume of a weak acid to the separated plasma in order to substantially dilute the concentration of immune complexes per unit of plasma and to reduce the pH of the diluted plasma sufficiently so that the immune complexes in the plasma will dissociate into respective antigens and antibodies;
removing the antigens from the plasma;
removing excess plasma fluid without removing substantial amounts of plasma protein so as to reduce the volume of plasma;
adding a basic material to the reduced volume of plasma so as to raise the pH of the reduced volume of plasma to a physiological pH;
mixing the reduced volume of plasma with the cellular blood components; and
returning the treated blood and antibodies contained therein to the patient.

22. A method for removing circulating antigens from a patient's circulatory system as defined in claim 21, wherein the weak acid comprises a solution containing hydrochloric acid.

23. A method for removing circulating antigens from a patient's circulatory system as defined in claim 21, wherein the pH of the separated plasma is reduced to about 3.1 in order to dissociate the immune complexes.

24. A method for removing circulating antigens from a patient's circulatory system as defined in claim 21, wherein a sufficient amount of acid solution is added to dilute the separated plasma by about 30 percent to about 70 percent.

25. A method for removing circulating antigens from a patient's circulatory system as defined in claim 24, wherein excess plasma fluid is removed following addition of the acid solution by passing the diluted plasma through ultrafiltration means capable of passing antigens together with fluid into the filtrate, but not capable of passing plasma proteins having a higher molecular weight.

26. A method for removing circulating antigens from a patient's circulatory system as defined in claim 25, wherein the plasma passing through the ultrafiltration means is passed through dialysis means to remove additional antigens.

27. A method for removing circulating antigens from a patient's circulatory system as defined in claim 26, wherein the dialysis means also serves to raise the pH of the plasma to a physiological level.

28. A method for removing circulating antigens from a patient's circulatory system as defined in claim 21, comprising the further step of adding a substantial amount of a dilution fluid to the patient's blood prior to separating a portion of the blood as plasma so that an increased percentage of the blood volume is separated as plasma during the plasma separation step.

29. A method for removing circulating antigens from a patient's circulatory system as defined in claim 21, comprising the further step of adding a substantial amount of a dilution fluid to the patient's blood prior to separating a portion of the blood as plasma so that a significant number of antigens bound to cellular blood components will become detached from such cellular blood components.

30. A method for removing circulating antigens from a patient's circulatory system as defined in claim 28, wherein a sufficient amount of dilution fluid is added to the blood so as to dilute the concentration of immune complexes per unit of blood to within the range of about 30 percent to about 70 percent of the concentration of immune complexes in the blood prior to dilution.

31. A method for removing circulating antigens from a patient's circulatory system as defined in claim 28 wherein the dilution fluid is a physiologically compatible electrolyte solution containing low molecular weight constituents of normal plasma.

32. A method for removing circulating antigens from a patient's circulatory system, comprising the steps of:
 obtaining from a patient blood containing immune complexes;
 diluting the blood prior to plasma separation by adding a dilution fluid containing low molecular weight constituents of plasma;
 separating from about 40 percent to about 60 percent of the diluted blood as a plasma fraction from the cellular components of the blood, said separated plasma containing immune complexes;
 diluting the plasma fraction by addition of an acid solution in order to substantially dilute the concentration of immune complexes per unit of plasma and also to reduce the pH of the diluted plasma sufficiently so that the immune complexes in the diluted plasma will dissociate into respective antigens and antibodies;
 removing excess plasma fluid without removing substantial amounts of plasma protein so as to reduce the volume of plasma and to simultaneously remove antigens;
 removing additional antigens from the reduced volume of plasma;
 adding a basic material to the reduced volume of plasma to raise the pH of thee reduced volume of plasma to a physilological pH;
 mixing the reduced volume of plasma with the cellular blood components; and
 returning the treated blood to the patient.

* * * * *

UNITED STATES PATENT AND TRADEMARK OFFICE
CERTIFICATE OF CORRECTION

PATENT NO. : 4,663,049

DATED : May 5, 1987

INVENTOR(S) : Willem J. Kolff et al.

It is certified that error appears in the above-identified patent and that said Letters Patent is hereby corrected as shown below:

Column 1, line 47, "to generate antibody" should be --to generate antibodies--
Column 2, line 26, "hepatatis" should be --hepatitis--
Column 2, line 63, "lymphooytes" should be --lymphocytes--
Column 4, line 10, "presetnly" should be --presently--
Column 4, line 25, "diseases" should be --diseases.--
Column 5, line 2, "cf" should be --of--
Column 6, line 41, "prefered" should be --preferred--
Column 7, line 36, "indioated" should be --indicated--
Column 7, line 66, "oause" should be --cause--
Column 8, line 47, "tc" should be --to--
Column 8, line 63, "parient's" should be --patient's--
Column 8, line 64, "destory" should be --destroy--
Column 11, line 66, "the blood" should be --in the blood--
Column 14, line 22, "thee" should be --the--
Column 14, line 23, "physilological" should be --physiological--

Signed and Sealed this

Twenty-fourth Day of November, 1987

Attest:

DONALD J. QUIGG

Attesting Officer

Commissioner of Patents and Trademarks